United States Patent [19]

Pimiskern

[11] Patent Number: 4,905,673

[45] Date of Patent: Mar. 6, 1990

[54] ARC DISCHARGE FOR SHOCK WAVE GENERATION

[75] Inventor: Klaus Pimiskern, Daisendorf, Fed. Rep. of Germany

[73] Assignee: Dornier System GmbH, Friedrichshafen, Fed. Rep. of Germany

[21] Appl. No.: 251,968

[22] Filed: Sep. 26, 1988

Related U.S. Application Data

[63] Continuation of Ser. No. 69,416, Jul. 1, 1987, abandoned.

[30] Foreign Application Priority Data

Jul. 3, 1986 [DE] Fed. Rep. of Germany ....... 3622352

[51] Int. Cl.[4] .............................................. A61B 17/22

[52] U.S. Cl. .................................................. 128/24 A

[58] Field of Search ............. 367/147; 128/639, 24 A, 128/653, 328

[56] References Cited

U.S. PATENT DOCUMENTS

| | | | |
|---|---|---|---|
| 2,559,227 | 7/1951 | Rieber | 128/24 A |
| 3,728,671 | 4/1973 | Poston, Jr. | 367/147 |
| 4,419,998 | 12/1983 | Heath | 128/639 |
| 4,608,983 | 9/1986 | Muller et al. | 128/328 |

FOREIGN PATENT DOCUMENTS

| | | | |
|---|---|---|---|
| 2635635 | 5/1979 | Fed. Rep. of Germany | 128/328 |

*Primary Examiner*—Ruth S. Smith
*Attorney, Agent, or Firm*—Ralf H. Siegemund

[57] ABSTRACT

Arc discharge for the production of shock waves for purposes of contactless, non-invasive comminution of concrements in the body of a living being, wherein the two electrodes have flattened tips of different diameter, the one leading to the inner conductor being larger, preferably by about 1.2:1.

4 Claims, 2 Drawing Sheets

ARC DISCHARGE FOR SHOCK WAVE GENERATION

This is a continuation of co-pending application Ser. No. 069,416 filed on July 01, 1987, now abandoned.

BACKGROUND OF THE INVENTION

The present invention relates to an arc discharge path for the generation of shock waves to be focused for non-invasive comminution of concrements in the body of a living being, whereby an arc is preferably produced under water, i.e. in a liquid coupling medium, and in-between two electrodes.

German patent 23 51 247, corresponding to U.S. Pat. No. 3,942,531, suggests a device for generating and focusing shock waves and generally describes procedures for the comminution of concrements, such as kidney stones without invasive surgery, the concrements being, of course, in the body of a living being. For a general discussion see, for example, Chaussy (ed) Extracorporeal Shock Wave Lithotripsy, Karger, 1982. Known and practiced devices of long successful standing include a focusing chamber being constructed as a partial rotational ellipsoid; a spark gap is provided for the production of an arc in one of the two focal points of such an ellipsoid; the other focal point is located in the concrement to be comminuted by focused shock waves. The shock waves, particularly as produced by arc discharge in the first one of the focal points propagates in all directions, and is reflected by the rotational ellipsoid and focused into the second focal point. The arc is preferably produced in a spark gap between two electrodes and upon discharge of an electrical capacitor so that a definite amount of electrical energy is converted into mechanical, shock wave energy. As the arc is fired in a very limited region, the rotational ellipsoid reflection permits a near point-like focusing of the shock wave with amplitudes being added to reach peaks in excess of 1 kbar, and for pulse durations below a micro second. Highly concentrated, strong, mechanical forces are, thus, concentrated in the concrement and readily destroy it resulting in a large number of small granules and fracture pieces which can be discharged from the body of the living being by natural processs.

German patent 26 35 636 discloses in greater detail electrodes of the type to which the invention pertains and for the particular purpose invisioned here; see also U.S. Pat. No. 4,608,983 of common assignee. A holder is provided and the electrodes project from that holder. One of the electrodes, so to speak, extends in a cage-like fashion over and beyond the particular focal point and doubles back in form of a loop, while the other electrode is directly oriented to face that point towards which the first mentioned electrode is doubled back, so that together and by means of their tips, they form a very small gap. These electrodes will face each other along an axis. One of the electrodes is, as stated, preferably constructed as a cage which carries a sleeve with a bore for fastening the electrode tip as a separate element. The cage maybe formed from two or more arc-shaped loops or the like. The other electrode just has a sleeve with a tip element in straight aligned fashion.

DESCRIPTION OF THE INVENTION

It is an object of the present invention to provide a new and improved arc discharge path under utilization of electrodes having features of improving their use life as compared with the known structures, and wherein, as time progresses, the focal point in which the arc is produce, moves and shifts very little so that a constant pressure obtains as a shock wave is generated.

In accordance with the prefered embodiment of the present invention, it is suggested to provide the two electrode tips, which face each other, with a different diameter and that the electrode tips are not point-like nor curved, but flattened, and that the diameter ratio between the two electrode tips is between 1.1:1 and 1.3:1, preferably about 1.2:1.

In order to obtain a high efficiency in the production of shock waves and the utilization of the shock waves for the comminution of concrements, it is necessary that the pressure in the shock wave amplitude remains as constant as possible. In other words, as time progresses, and for different pulses and assuming, of course, constant electrical discharge values as far as the triggering and powering capacitor is concerned. The locus of arc development will remain invariant in the first focal point. The accuracy is required since the reflector geometry is such that the focusing of the shock waves for use in the second focal point will be optimized only if, in fact, the shock waves are nearly spherically symmetrical produced as they eminate from the first focal point as geometric point of origin. Every small shifts of the discharge path relative to first focal point and for any reason, for example, owing to different wear on the electrodes, causes defocusing as far as the second focal point is concerned, which means that the concentration of shock wave energy is no longer optimized and that, as time progresses, renders increasingly doubtful that the concrements are, in fact, comminuted in an optimized fashion or even comminuted at all. The invention, as suggested here, provides for a means that permits maintaining shifting of the arc generation vis-a-vis the first focal point to be much smaller than in conventional electrode systems.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantage thereof will be better understood from the following description taken in connection with the accompanying drawings in which:

Proceeding now to the detailed description of the drawings, FIG. 1 illustrates an arc discharge path between a first electrode tip 4 and a second electrode tip 6 along an axis 2. Herein, electrode tip 4 is the so-called outer electrode and electrode tip 6 pertains to the inner electrode, that is to say electrode tip 6 is, so to speak, the end of an inner conductor 16 of a coaxial system and electrode tip 4 is the end of an outer, concentric electrode 10. In accordance with the invention, as can be seen, the diameters of the two effective faces of the electrode tips, as they are facing each other, are not equal and have to follow certain rules. In particular, the electrode face of the outer electrode tip 4 has a smaller diameter than the face of the inner electrode 6. Consequently, the two electrodes burn off differently. As long as per prior art practice these diameters are equal, it is clear that certain tolerance deviations occur. In fact, in an unfavorable situation (not recognized as such by the art) the diameter of the inner conductor electrode is a little smaller than the diameter of the outer conductor electrode. In such a situation, the discrepancy between the two burn-off situations is very unfavorably large. If, however, the radii of inner and outer conductor electrode tips are such that the outer eletrode tip has definitely a smaller diameter than the inner electrode tip, and in particular, the radii or diameter approach the value of 1.2, then it was found that under these unequal circumstances the two electrodes burn off approximately at the same rate.

Figure 1:
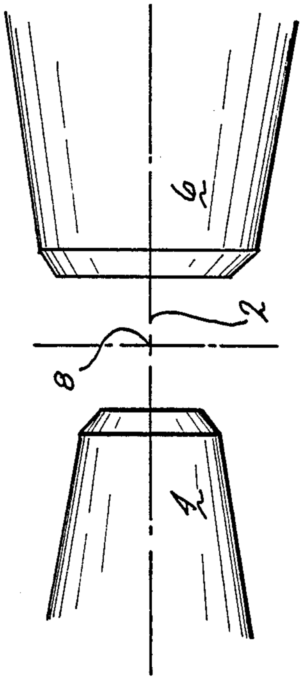
FIG. 1 is a highly enlarged arc discharge and spark gap area including electrode tips constructed in accordance with the preferred embodiment of the present invention for practicing the best mode thereof.

These aspects should be considered in some detail. For the same tip diameter the burn off of the inner conductor, particularly its inner electrode tip area, is about 1.2× larger than the burn off electrode tip area of the outer conductor. The average unit areal burn off of the inner conductor electrode (cathode 6) occurs from 30 to 50% faster than at the outer electrode (anode 4). However, the diameter of the inner conductor electrode tip 6 is increased in accordance with the invention and, as stated, at an ideal ratio to be somewhere in the value between 1.1:1 and 1.3:1. Now, the burn off is equalized.

The focal point 8 of this system is, at least initially, situated precisely in the center between the two electrodes. Owing to the matched diameter of the electrodes, they will, in fact, burn evenly, and, therefore, even for a large number of produced shock waves, the focal point 8 will remain in that central location. The edges of the electrode tips 4 and 6 should be deburred on making, through drum grinding, in order to avoid any sharp edges and true points where arcs could parasitically discharge, in an asymmetric fashion, bypassing the focal point 8. In fact, the electrode tips 4 and 6 should be very flat, they are, in fact, as shown, of a double-trunketed cone configuration.

The trunketed cone in the tip area has an apex angle of about 20°, the conical contour of the body is a much more acute. The tips can be geometrically reproduced much better than conventional rounded peaks or tips. The tolerance range, in case of rounded tips, is hardly better ±0.1 mm. The flattened tips proposed here have a tolerance which can be reduced with a ±0.02 mm, i.e. better by a factor of 5. Small tolerances in the manufacture, however, means automatically a higher degree of reproducability as far as specific shock waves and shock wave contours and patterns are concerned, and, therefore, ensures constant pressure in the peak and focus areas over a long period of time. A particular example of the preferred configuration as far as the electrode tips are concerned, is as follows. The inner electrode tip 6 has a diameter of 1.0±0.02 mm, and the outer electrode tip 4 has a diameter of 0.8±0.02 mm.

Figure 2:
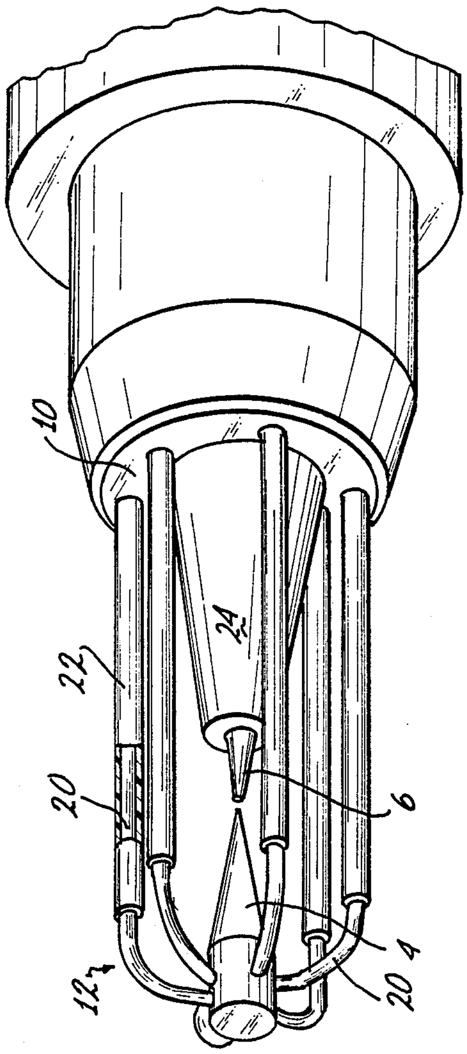
FIG. 2 is a perspective view of an electrode system which includes the inventive electrode tips.
Figure 3:
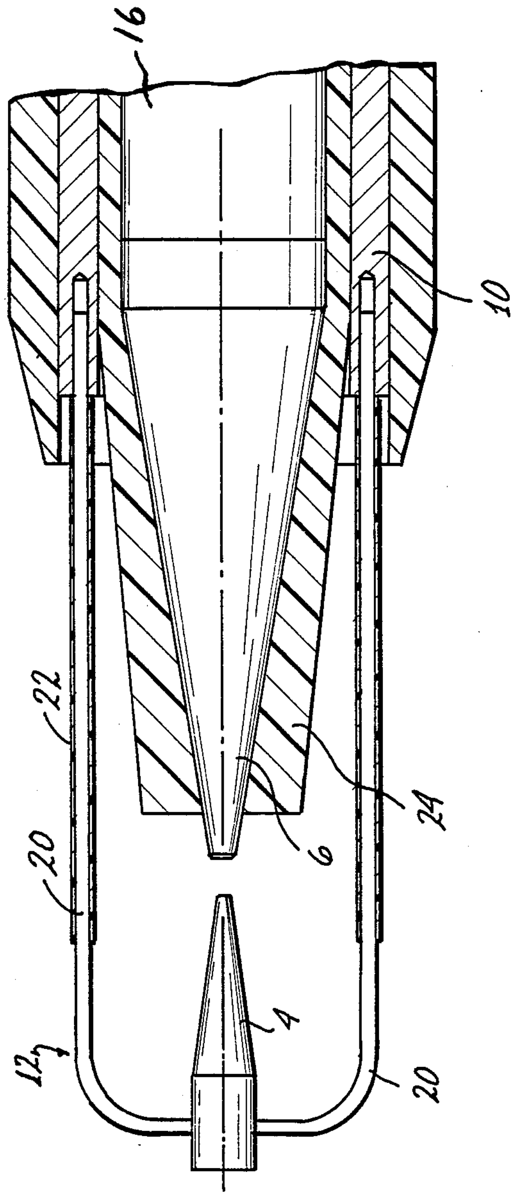
FIG. 3 is a cross-section as indicated in FIG. 2, showing structure on a scale that is in-between the scale shown in FIG. 1 and FIG. 2.

FIGS. 2 and 3 now show advantageous configurations in which, so to speak, the invention is embedded. There is shown a tubular outer conductor 10 which is continued in a cage 12, being comprised of several metallic loops 20. This construction is by and in itself similar to German patent No. 26 35 635 which is self-explanatory from the drawings of that patent. Related applications of common assignee are Ser. Nos. 940,023, filed Dec. 1, 1986; and 917,854, filed Oct. 14, 1986. The electrode 4 is directly welded to the loop 20 which, in turn, are insulated by synthetic cover or sleeves 22. Electrode tip 6, on the other hand, is held by means of an attenuator 24 in and on the assembly. The attenuator 24 is made of a synthetic material.

Flat tips of the electrodes reduce also the diameter tolerances and, therefore, are advantageous as far as reproducability of the manufactured part is concerned. Specifically differing diameters for inner and outer electrode tips guarantee a noticeably longer use life of the electrodes, a smaller shift of the arc generating point vis-a-vis focal point 8, and, therefore, an improved pressure distribution in the shock waves and consistency in contents of pressure for sequential pressure waves. Also, the focusing is more adequate in the second focal point of the rotational ellipsoid and, therefore, the result is a highly effective comminution of concrements.

The invention is not limited to the embodiments described above, but all changes and modifications thereof, not constituting departures from the spirit and scope of the invention are intended to be included.

I claim:

1. An arc discharge device for a submerged production of shock waves for purposes of contactless, non-invasive comminution of concrements in the body of a living being, including an electrode assembly having an inner electrode and an outer electrode; for obtaining an arc discharge between them, further including an inner and an outer conductor connected to the assembly in that the inner electrode extends from the inner conductor and the outer electrode is mounted on the outer conductor and extends towards the inner conductor, for applying a voltage to electrodes of the assembly to obtain the arc discharge between them, the improvement comprising:

the two electrodes having tips of initially different diameter, the tips being flattened and face each other, the diameter of inner electrode being initially larger than the diameter of the tip of the outer electrode.

2. An arc discharge device as in claim 1, the diameter ratio of the two electrodes being from 1.1:1 to 1.3:1.

3. An arc discharge device for a submerged production of shock waves for purposes of contactless, non-invasive comminution of concrements in the body of a living being, including an electrode assembly comprising an inner and an outer electrode for obtaining an arc discharge between them, further including an inner and an outer conductor connected to the assembly, the inner electrode extending from the inner conductor and the outer electrode is mounted on the outer conductor, and extends towards the inner conductor for applying a voltage to the electrodes to obtain the arc discharge, the improvement comprising:

each of the electrodes having a tip, the diameter of the tip of the inner electrode being initially larger than the diameter of the tip of the outer electrode, the tips facing each other.

4. An arc discharge device as in claim 3, the diameter ratio of the two electrodes being from 1.1:1 to 1.3:1.

* * * * *